United States Patent
Takasu

(10) Patent No.: US 9,952,131 B2
(45) Date of Patent: Apr. 24, 2018

(54) MEASUREMENT DEVICE AND METHOD OF MEASURING

(71) Applicant: FUJITSU LIMITED, Kawasaki-shi, Kanagawa (JP)

(72) Inventor: Ryozo Takasu, Isehara (JP)

(73) Assignee: FUJITSU LIMITED, Kawasaki (JP)

( * ) Notice: Subject to any disclaimer, the term of this patent is extended or adjusted under 35 U.S.C. 154(b) by 0 days.

(21) Appl. No.: 14/712,168

(22) Filed: May 14, 2015

(65) Prior Publication Data
US 2015/0346071 A1 Dec. 3, 2015

(30) Foreign Application Priority Data
May 28, 2014 (JP) ................................. 2014-110058

(51) Int. Cl.
*G01N 15/06* (2006.01)
*G01N 5/02* (2006.01)
*G01N 15/00* (2006.01)

(52) U.S. Cl.
CPC ............. *G01N 15/06* (2013.01); *G01N 5/02* (2013.01); *G01N 15/0606* (2013.01); *G01N 2015/0046* (2013.01); *G01N 2015/0693* (2013.01)

(58) Field of Classification Search
CPC ...... G01N 5/02; G01N 15/06; G01N 15/0606; G01N 2015/0046; G01N 2015/0693
USPC ............. 73/28.01, 23.2, 24.06; 356/337–343
See application file for complete search history.

(56) References Cited

U.S. PATENT DOCUMENTS

| 5,571,945 A | 11/1996 | Koutrakis |
| 5,572,322 A | 11/1996 | Noda |

FOREIGN PATENT DOCUMENTS

| CN | 202837148 U | 3/2013 | |
| GB | 2506991 A | * 4/2014 | ......... G01N 15/0272 |
| JP | H08-15122 | 1/1996 | |
| JP | H11-502303 | 2/1999 | |
| JP | 2006-003090 A | 1/2006 | |
| WO | 99/018425 A1 | 4/1999 | |

OTHER PUBLICATIONS

Non-Patent Literature "Mass Calibration and Relative Humidity Compensation Requirements for Optical Portable Particulate Matter Monitors: The IMPASHS (Impact of Smoke-free Policies in EU Member States)", A. A. Reprecht et. al., Epidemiology 22(1):S206, p. 179-196, Jan. 2011, doi: 10.1097/01.ede.0000392314.24613.c6.*
Non-Patent Literature "Heating Effects on Integrating Nephelometer Measurement", Lu-Yen Chen et. al., J. Enviorn. Eng. Manage., 18(5), 339-344 (2008).*
Bam 1020 Particulate Monitor Operation Manual BAM-1020-9800 Rev H, 2008, accessed at https://www.arb.ca.gov/airwebmanual/instrument_manuals/Documents/BAM-1020-9800_Manual_Rev_H.pdf.*

(Continued)

*Primary Examiner* — Peter Macchiarolo
*Assistant Examiner* — Irving A Campbell
(74) *Attorney, Agent, or Firm* — Kratz, Quintos & Hanson, LLP

(57) ABSTRACT

A measurement device includes: a mass measurer that measures a mass of particles in gas; a humidity changer that changes a humidity of atmosphere to which the particles are exposed; and a calculator that calculates information indicating a correlation of the mass with respect to the humidity.

9 Claims, 13 Drawing Sheets

(56) References Cited

OTHER PUBLICATIONS

Office Action of Japanese Patent Application No. 2014-110058 dated Dec. 19, 2017 (4 Sheets, 4 Sheets translation, 8 Sheets total).
Chinese Patent Application No. 201510259817.5: Notification of the First Office Action dated Jul. 21, 2017.

* cited by examiner

MEASUREMENT DEVICE AND METHOD OF MEASURING

CROSS-REFERENCE TO RELATED APPLICATION

This application is based upon and claims the benefit of priority of the prior Japanese Patent Application No. 2014-110058, filed on May 28, 2014, the entire contents of which are incorporated herein by reference.

FIELD

A certain aspect of embodiments described herein relates to a measurement device as a method of measuring.

BACKGROUND

Recently, concentration measurements of particulate substances such as PM 2.5 are frequently performed. A mass of particles in gas per a unit volume is used as a concentration unit of particles in gas. The particles concentration is a mass concentration. There is a method of collecting particles of gas into a filter and measuring a mass of the particles as a standard method of measuring the mass concentration of the PM 2.5 (for example, see Japanese Patent Application Publication No. 11-502303). There is a beta-ray absorption method as a method of measuring a mass concentration that can be automatically performed. The concentration obtained by the filtering method or the beta-ray absorption method is a mass concentration. Presently, the PM 2.5 concentration is generally expressed as the mass concentration. Moreover, there is a method of light-scattering detection method of measuring the number of particles in gas with use of a scattered light obtained by radiating a light to the particles in the gas, as a simple method.

SUMMARY

According to an aspect of the present invention, there is provided a measurement device including: a mass measurer that measures a mass of particles in gas; a humidity changer that changes a humidity of atmosphere to which the particles are exposed; a calculator that calculates information indicating a correlation of the mass with respect to the humidity.

According to another aspect of the present invention, there is provided a measurement device including: a concentration measurer that measures a number concentration of particles in gas; and a calculator that calculates a mass concentration of particles in gas based on information indicating a correlation of a humidity of the particles with respect to a humidity of atmosphere to which the particles are exposed and the number concentration measured by the concentration measurer.

According to another aspect of the present invention, there is provided a method of measuring comprising: measuring a number concentration of particles in gas; and calculating a mass concentration of particles in gas based on information indicating a correlation of a humidity of the particles with respect to a humidity of atmosphere to which the particles are exposed and the number concentration measured by the measuring.

DESCRIPTION OF EMBODIMENTS

For example, it takes 24 hours or more to perform a single measuring with use of the method of collecting particles with a filter. Moreover, an automatic measuring is difficult. On the other hand, an automatic measuring is possible with respect to the beta-ray absorption method. However, the measuring time is not sufficiently short. A measurement device is large and expensive. With respect to the light-scattering method, an automatic measuring is possible and a measurement time is short. And, a downsizing of a measurement device is possible and the measurement device is not expensive. However, the concentration that can be measured by the light-scattering method is not a mass concentration but a number concentration corresponding to the number of particles in a unit volume. Therefore, accuracy may be degraded during converting the number concentration into the mass concentration.

A concentration that can be measured by a light-scattering method is not a mass concentration but a number concentration corresponding to the number of particles per a unit volume. Humidity of gas has an effect on converting of the number concentration of particles in gas into the mass concentration. For example, when the humidity of the gas changes, a moisture absorption amount of particles also changes. Therefore, a distribution of particles diameters and physicochemical characteristics change. Particles are mixtures of various components. Moisture absorption characteristics of particles differ in accordance with components of particles. For example, when the particles are ammonium sulfates, a cross section area of light scattering at 90% humidity is five times as that in a dried condition. When the particles are organic substances, the humidity has little influence on the cross section area of light scattering. In this manner, when the components of the particles change, moisture absorption characteristics of the particles also change. The components of the particles change in accordance with a place and a time. Therefore, the accuracy of the conversion of the number concentration into the mass concentration becomes lower. In the following embodiments, the accuracy of the conversion of the number concentration of particles into the mass concentration becomes higher by simply measuring the moisture absorption characteristic of the particles. It is thereby possible to measure the concentration of particles with high accuracy.

First Embodiment

Figure 1:
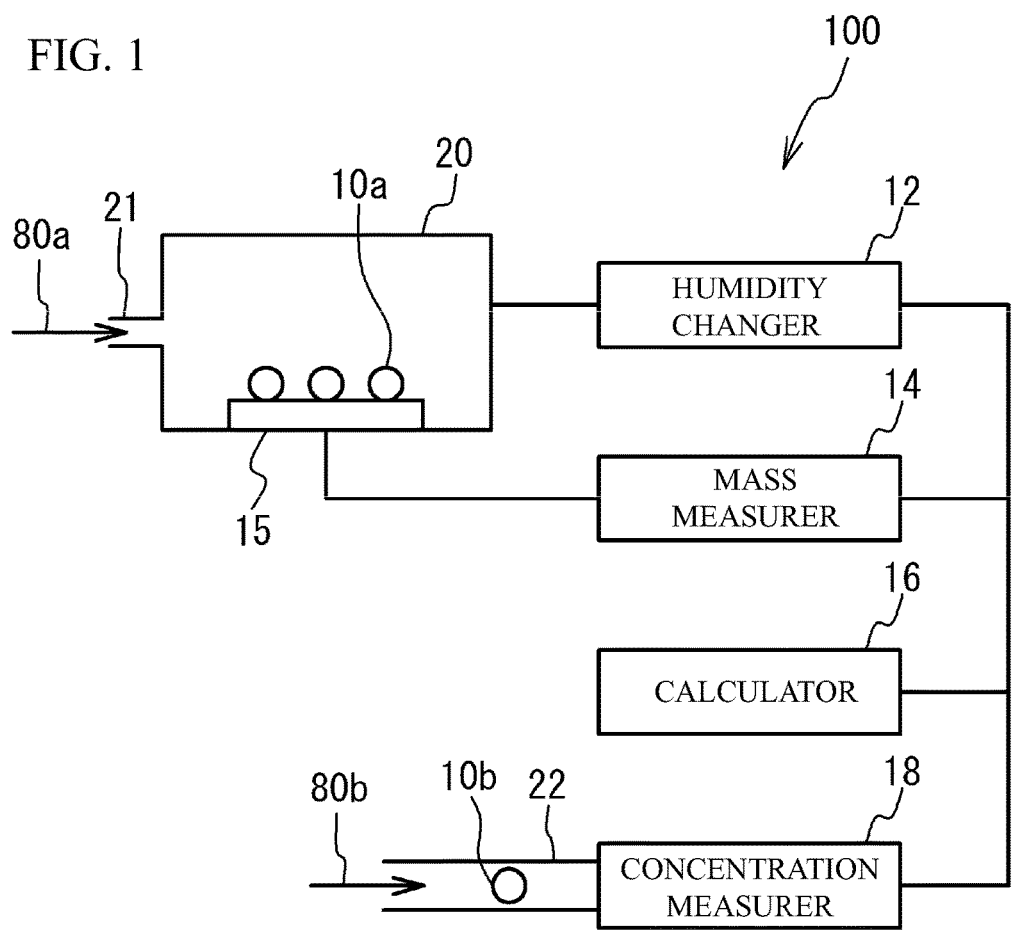
FIG. 1 illustrates a block diagram of a measurement device in accordance with a first embodiment.
Figure 2:
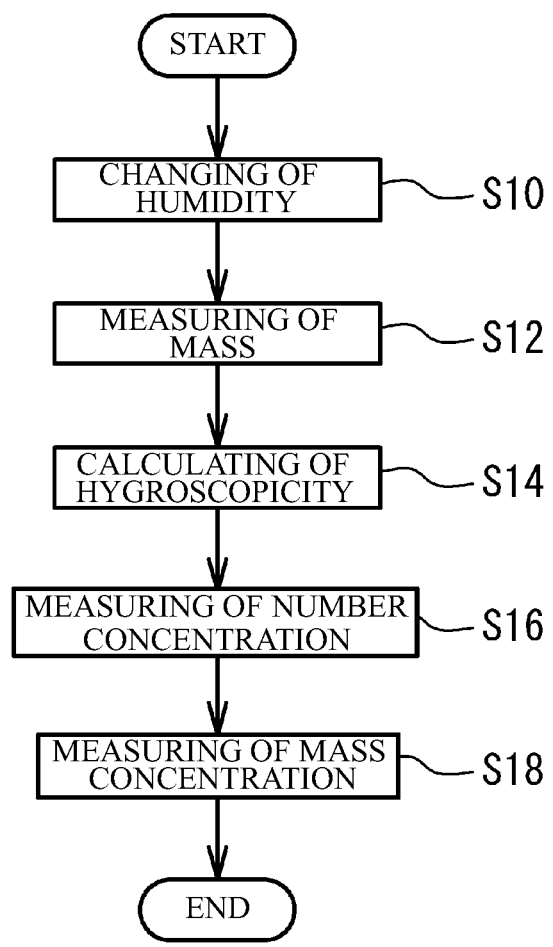
FIG. 2 illustrates a flowchart of a method of measuring in accordance with a first embodiment.

FIG. 1 illustrates a block diagram of a measurement device in accordance with a first embodiment. FIG. 2 illustrates a flowchart of a method of measuring in accordance with the first embodiment. As illustrated in FIG. 1 and FIG. 2, a measurement device 100 mainly has a humidity changer 12, a mass measurer 14, a calculator 16, a concentration measurer 18 and a measurement tank 20. An inlet 21 guides gas 80a such as atmospheric air into the measurement tank 20. Particles 10a in the gas 80a adhere to a stage 15. The humidity changer 12 changes humidity of atmosphere to which the particles 10a in the measurement tank 20 are exposed (Step S10). The mass measurer 14 measures a mass of the particles 10a in the gas 80a adhered to the stage 15 (Step S12). The calculator 16 calculates a hygroscopic parameter from a relative humidity of atmosphere around the particles 10a and the mass of the particles 10a (Step S14). The hygroscopic parameter is information indicating a correlation of a mass with respect to humidity.

After that, gas 80b is guided into the concentration measurer 18 via an inlet 22. Components of particles 10b in the gas 80b are approximately the same as those of the particles 10a of the gas 80a. For example, places and/or timings of collection of the gas 80a and the gas 80b are approximately identical. The concentration measurer 18 measures a number concentration of the particles 10b in the gas 80b (Step S16). In this case, humidity of the gas 80b is also measured, simultaneously with the measuring of the number concentration. The calculator 16 calculates a mass concentration of the particles 10b in the gas 80b from the number concentration measured by the concentration measurer 18, the hygroscopic parameter and the humidity of the gas 80b (Step S18).

In the first embodiment, as in the case of the step S14, the calculator 16 calculates the hygroscopic parameter of the particles 10a having components similar to those of the particles 10b in the gas 80b subjected to the measurement of the number concentration. As in the case of the step S18, the mass concentration of the particles 10b of the gas 80b is calculated from the hygroscopic parameter of the particles 10a, the number concentration of the particles 10b of the gas 80b and the humidity of the gas 80b. In this manner, the measurement device 100 is capable of measuring the concentration of the particles 10b with high accuracy and in a short time by calculating the mass concentration of the particles 10b in view of the hygroscopicity of the particles 10b.

Second Embodiment

Figure 3:
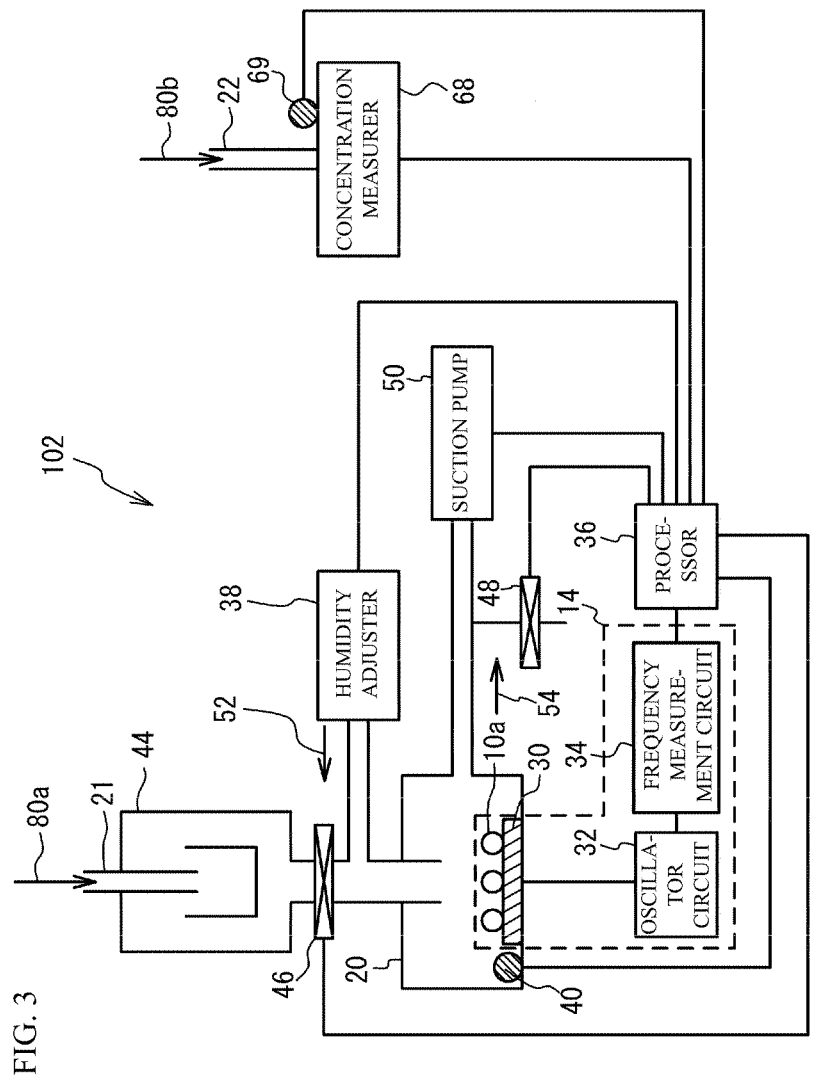
FIG. 3 illustrates a block diagram of a measurement device in accordance with a second embodiment.

A second embodiment is a concrete example of the first embodiment. FIG. 3 illustrates a block diagram of a measurement device in accordance with the second embodiment. A measurement device 102 mainly has a humidity adjuster 38, the mass measurer 14, the measurement tank 20, a processor 36, an impactor 44, a suction pump 50 and a concentration measurer 68 of light scattering type. The humidity adjuster 38 corresponds to the humidity changer 12 of the first embodiment. A hygrothermal sensor 40 to measure a temperature and humidity in the measurement tank 20 is provided in the measurement tank 20. The mass measurer 14 is a microbalance and has a quartz crystal oscillator 30, an oscillator circuit 32, and a frequency measurement circuit 34. The concentration measurer 68 of light scattering type corresponds to the concentration measurer 18 of the first embodiment.

The inlet 21 breaths the atmospheric gas as the gas 80a. The impactor 44 separates the particles 10a in the gas 80a having sizes within a desirable range. For example, when the impactor 44 measures a concentration of PM 2.5, the impactor 44 separates particles of which size (diameter in a case where particles are spherical) is approximately 2.5 μm or less. The sizes of the particles 10a separated by the impactor 44 can be determined arbitrarily. For example, the sizes may be 10 μm or less. An isolation valve 46 opens and closes between the impactor 44 and the measurement tank 20. The particles 10a are collected to a surface of the quartz crystal oscillator 30. The quartz crystal oscillator 30 and an oscillator circuit 32 under the quartz crystal oscillator 30 work together and transmit a signal. A frequency of the oscillation signal corresponds to the mass of the quartz crystal oscillator 30 including the particles 10a. The frequency measurement circuit 34 measures an oscillation frequency. The humidity adjuster 38 humidifies air or dehumidifies air, and thereby intakes (52) gas having adjusted humidity into the measurement tank 20. The suction pump 50 exhausts (54) the gas in the measurement tank 20. An exhaust valve 48 opens and closes between the measurement tank 20 and the atmospheric air.

The processor 36 corresponds to the calculator 16 of the first embodiment and is a computer, a processor or the like. The processor 36 outputs a signal for adjusting humidity that orders humidity to the humidity adjuster 38. The processor 36 outputs an on/off signal ordering on or off to the suction pump 50. The processor 36 outputs a signal for opening or closing that orders opening or closing to the valves 46 and 48. The processor 36 obtains frequency information indicating a measured frequency from the frequency measurement circuit 34. The processor 36 obtains hygrothermal information indicating a temperature and humidity in the measurement tank 20 from the hygrothermal sensor 40. The hygrothermal sensor may be a humidity sensor. The hygrothermal information may be humidity information indicating humidity. The processor 36 calculates the mass of the particles 10a from the frequency information. The processor 36 calculates the hygroscopic parameter of the particles 10a from the humidity information and the calculated mass.

The inlet 22 breathes the atmospheric air as the gas 80b. The concentration measurer 68 of light scattering type measures a number concentration of particles in the gas 80b with use of a light scattering method. A humidity sensor 69 (humidity measurer) measures a relative humidity of the gas 80b (atmosphere to which the particles 10b subjected to the number concentration measurement are exposed), simultaneously with the measurement of the number concentration by the concentration measurer 68 of light scattering type. The processor 36 outputs a signal ordering measurement to the concentration measurer 68 of light scattering type. And, the processor 36 obtains the number concentration of the particles in the gas 80b from the concentration measurer 68 of light scattering type. The processor 36 obtains the relative humidity of the gas 80b from the humidity sensor 69. The processor 36 calculates the mass concentration of the particles 10b in the gas 80b based on the number concentration that is obtained from the concentration measurer 68 of light scattering type, the relative humidity that is obtained from the humidity sensor 69 and the hygroscopic parameter of the particles 10b.

The inlet 21 and the inlet 22 may be common. However, it is preferable that the inlet 21 and the inlet 22 are separately provided in order to suppress a loss of the particles 10a and the particles 10b at a branch portion of a pipe. The processor 36 calculates the hygroscopic parameter and the mass concentration. However, the calculation of the hygroscopic parameter and the calculation of the mass concentration may be separately performed by different processors.

Figure 4:
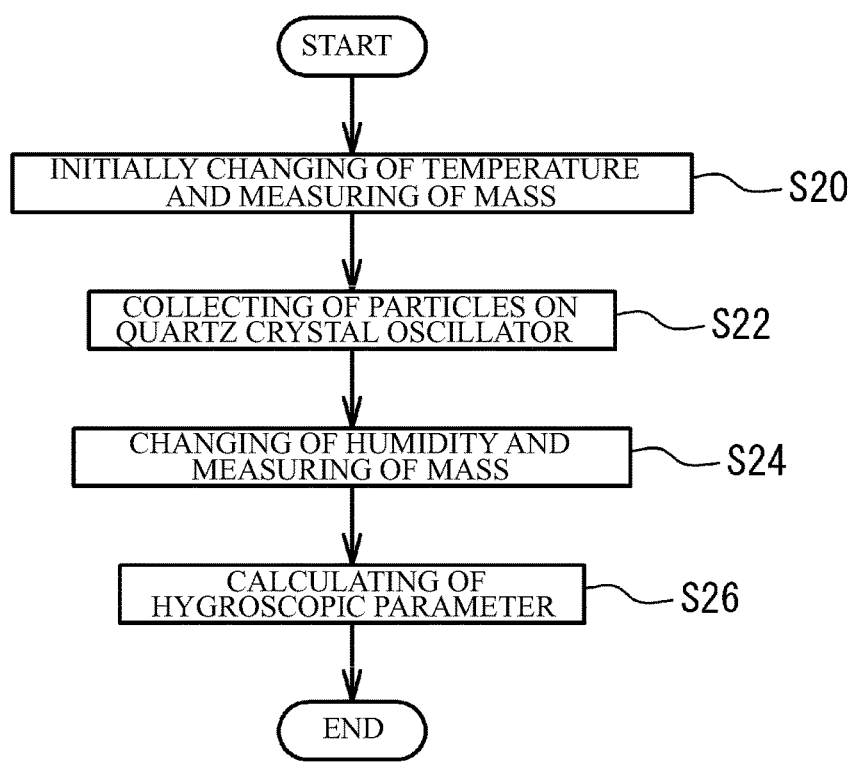
FIG. 4 illustrates a flowchart of processes performed by a processor in a second embodiment.

FIG. 4 illustrates a flowchart of processes performed by the processor in the second embodiment. As illustrated in FIG. 4, the processor 36 orders the humidity adjuster 38 to change the humidity in the measurement tank 20 and orders the mass measurer 14 to measure the mass of the quartz crystal oscillator 30, before providing the particles 10a into the measurement tank 20 (step S20). The processor 36 orders the valves 46 and 48 and the suction pump 50 to collect the particles 10a to the surface of the quartz crystal oscillator 30 (step S22). The processor 36 orders the humidity adjuster 38 to change the humidity in the measurement tank 20 and orders the mass measurer 14 to measure the mass of the quartz crystal oscillator 30 including the particles 10a (step S24). The processor 36 calculates the hygroscopic parameter of the particles 10a based on the measurement results of the step S20 and the step S24 (step S26).

Figure 5:
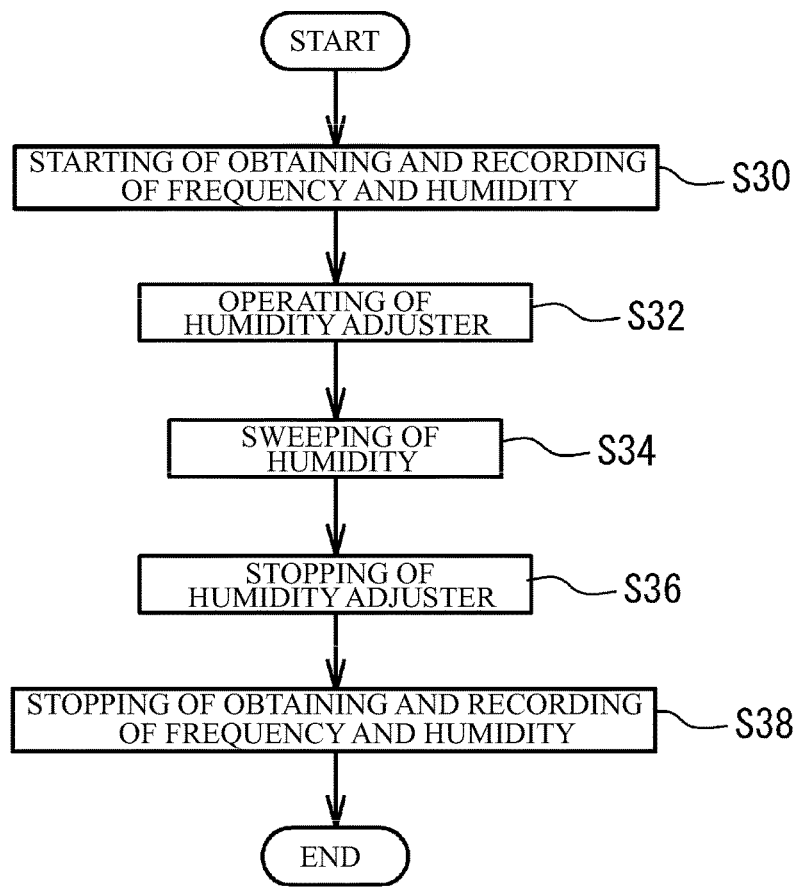
FIG. 5 illustrates a flowchart of processes of a processor in steps S20 and S24 of FIG. 4.

FIG. 5 illustrates a flowchart of the processes of the processor in the step S20 and the step S24 of FIG. 4. As illustrated in FIG. 5, the processor 36 starts obtaining frequency information and humidity information. The processor 36 starts recording the frequency information and the humidity information (step S30). The frequency information and the humidity information at an identical time are associated with each other and are recorded. The processor 36 operates the humidity adjuster 38 (step S32). The processor 36 makes the humidity adjuster 38 sweep the humidity of gas provided to the measurement tank 20 (step S34). The processor 36 stops the humidity adjuster 38 (step S36). The processor 36 stops the obtaining and the recording of the frequency information and the humidity information (step S38).

Figure 6:
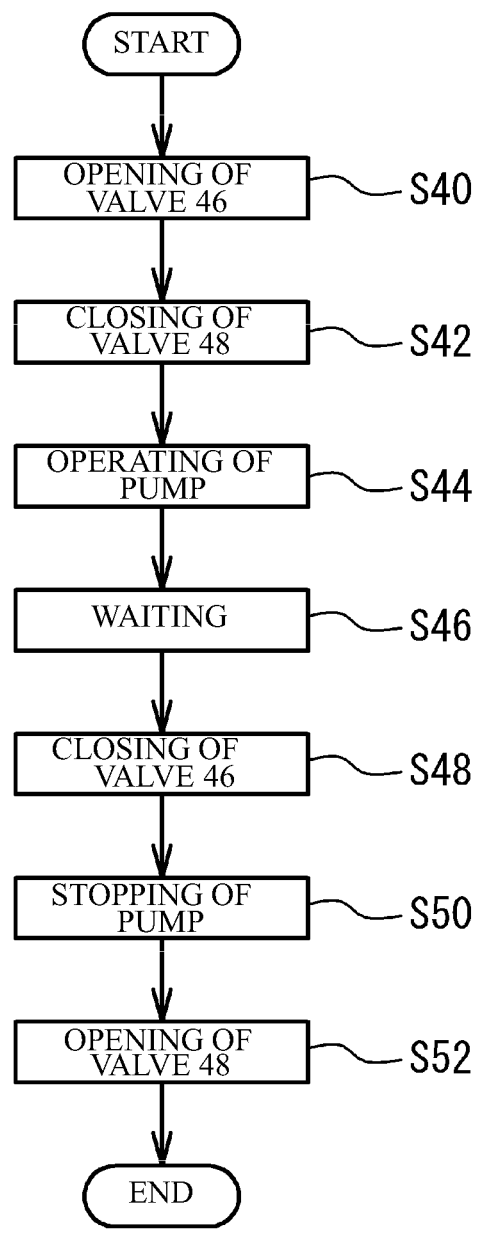
FIG. 6 illustrates a flowchart of processes of a processor in step S22 of FIG. 4.

FIG. 6 illustrates a flowchart of the processes of the processor in the step S22 of FIG. 4. As illustrated in FIG. 6, the processor 36 opens the isolation valve 46 (step S40). The processor 36 closes the exhaust valve 48 (step S42). The processor 36 operates the suction pump 50 (step S44). With the processes, the particles 10a that are separated by the impactor 44 and have predetermined sizes are provided into the measurement tank 20. The processor 36 waits for a predetermined time (step S46). Thus, the gas 80a having a predetermined volume passes through the measurement tank 20, and the particles 10a are collected to the surface of the quartz crystal oscillator 30. After that, the processor 36 stops the suction pump 50 (step S50). The processor 36 opens the exhaust valve 48 (step S52). With the processes, the collecting of the particles 10a is terminated.

Figure 7A:
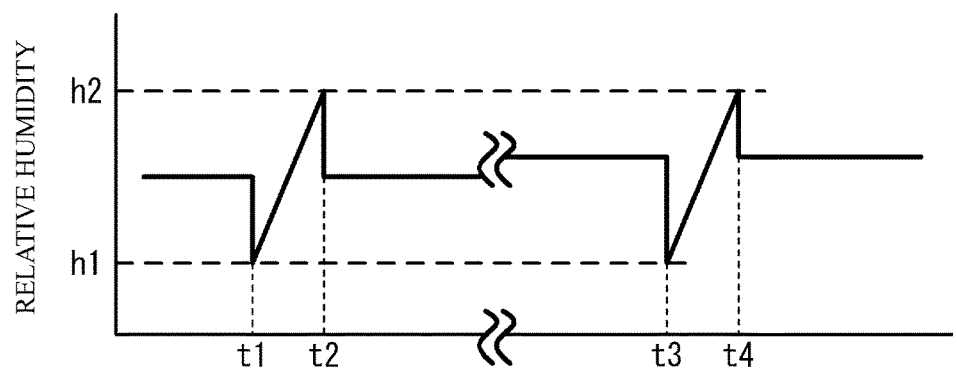
FIG. 7A and FIG. 7B respectively illustrate relative humidity in a measurement tank and a mass of a quartz crystal oscillator with respect to an elapsed time.
Figure 7B:
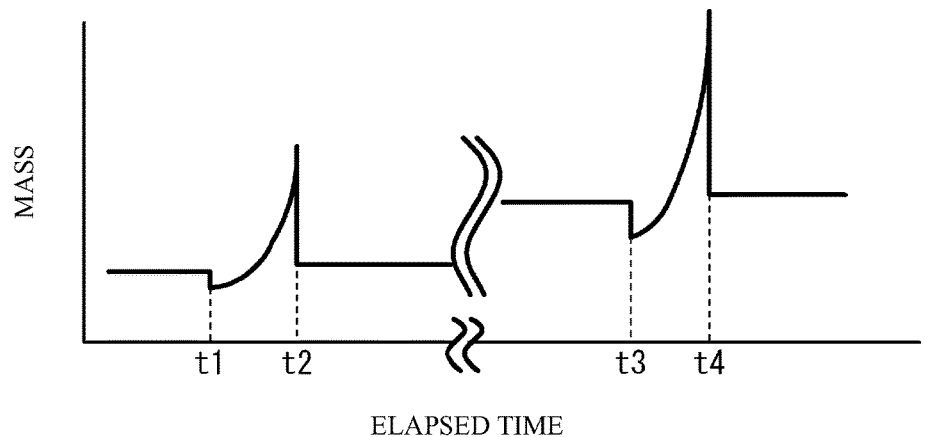

FIG. 7A and FIG. 7B respectively illustrate the relative humidity in the measurement tank and the mass of the quartz crystal oscillator with respect to an elapsed time. As illustrated in FIG. 7A and FIG. 7B, until a time t1, the humidity in the measurement tank 20 is not adjusted, and the humidity in the measurement tank 20 is not constant. The mass of the quartz crystal oscillator 30 is a given value. From the time t1 to a time t2, the measuring of the step S20 is performed. At the time t1, the humidity adjuster 38 starts to change the humidity in the measurement tank 20. The humidity in the measurement tank 20 at the time t1 is h1. The humidity gradually changes from the time t1 to the time t2. The humidity at the time t2 is h2. With the changing of the humidity, the humidity of the quartz crystal oscillator 30 changes. This is because the surface of the quartz crystal oscillator 30 and/or dust adsorbed to the surface absorb moisture.

From the time t2 to the time t3, the particles 10a are collected on the quartz crystal oscillator 30 as in the case of the step S22. Just before the time t3, the humidity is not constant. The mass of the adsorption amount of the particles 10a is added to the mass. From the time t3 to the time t4, the measuring of the step S24 is performed. From the time t3 to the time t4, the relative humidity in the measurement tank 20 continuously changes from h1 to h2. With the changing of the humidity, the mass of the quartz crystal oscillator 30 changes.

The humidity h1 and the humidity h2 are for example, respectively 0% and 100%. The relative humidity h1 may be humidity (for example, 10%) such that the adsorption of water can be ignored. The relative humidity h2 may be maximum humidity that occurs in a condition for measuring the concentration of particles. In this manner, the relative humidity h1 and the relative humidity h2 can be set arbitrarily.

Figure 8A:
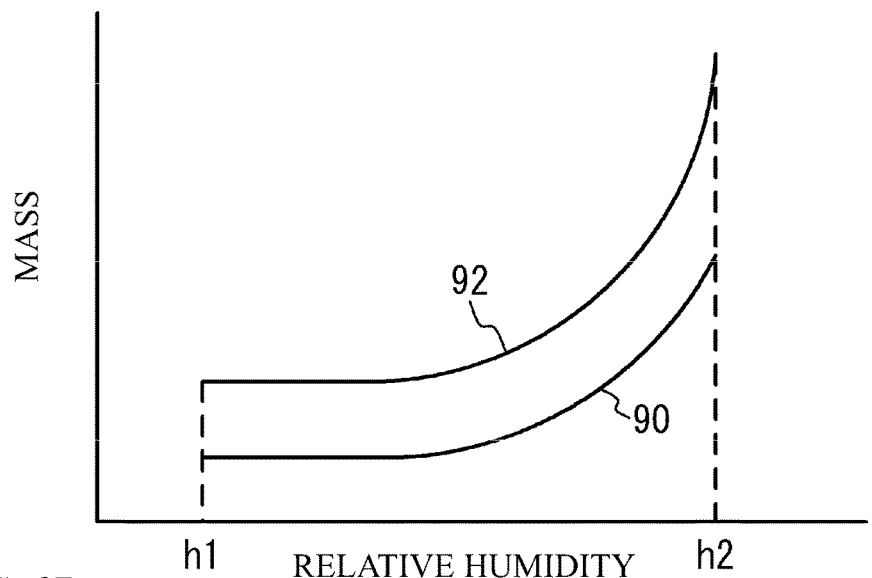
FIG. 8A to FIG. 8C illustrate a mass with respect to relative humidity.
Figure 8B:
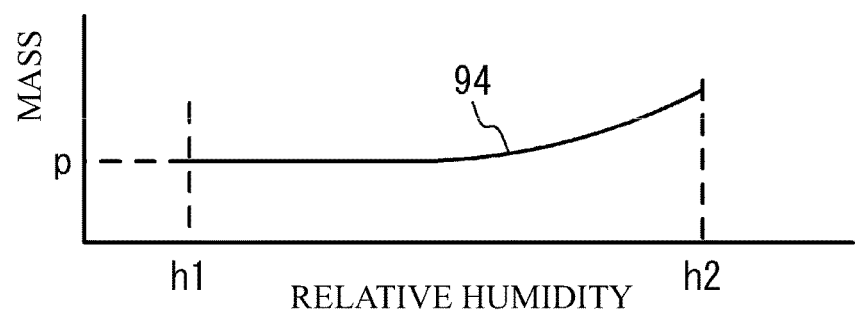
Figure 8C:
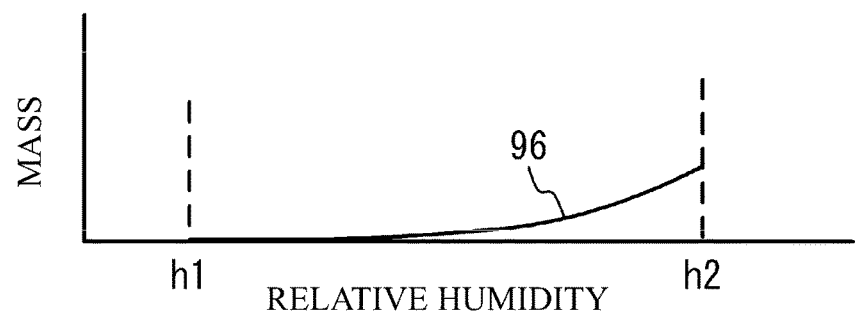

FIG. 8A to FIG. 8C illustrate the mass with respect to the relative humidity. As illustrated in FIG. 8A, the processor 36 calculates a correlation curve 90 of the mass with respect to the relative humidity in a period from the time t1 to the time t2 based on FIG. 7A and FIG. 7B. The processor 36 calculates a correlation curve 92 of the mass with respect to the relative humidity in a period from the time t3 to the time t4. As illustrated in FIG. 8B, the processor 36 makes a curve 94 by subtracting the curve 90 from the curve 92. The curve 94 indicates the mass in which the mass of the particles 10a adsorbed to the quartz crystal oscillator 30 is added. The mass p at the humidity h1 at which there is little adsorption of water to the particles 10a corresponds to the mass of the particles 10a to which water is not adsorbed. As illustrated in FIG. 8C, the processor 36 calculates a curve 96 by subtracting the mass p from the curve 94. The curve 96 corresponds to the increasing mass caused by the moisture absorption of the particles 10a. A value obtained by dividing the curve 96 by the mass p is a hygroscopic parameter a(h) per a unit mass. The hygroscopic parameter a(h) is a mass of water absorbed by dried particles per a unit mass at the humidity h.

In the second embodiment, as illustrated in FIG. 3, the mass measurer 14 includes the quartz crystal oscillator 30 to which the particles 10a are adsorbed. It is therefore possible to measure the mass and the changing of the mass of the particles 10a with high accuracy. As illustrated in FIG. 7A, the humidity adjuster 38 changes the humidity gradually. Thus, it is possible to continuously measure the changing of the mass with respect to the humidity.

Figure 9:
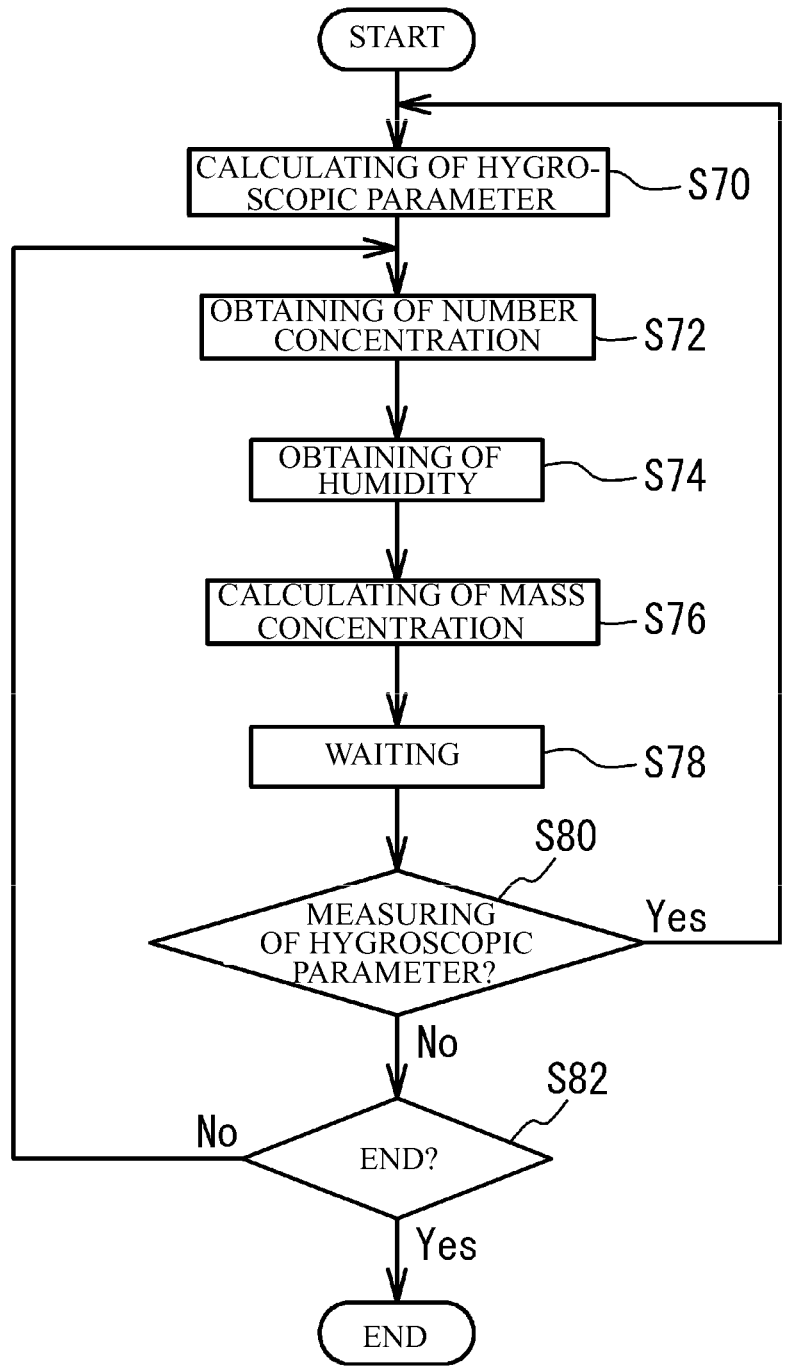
FIG. 9 illustrates a flowchart of an operation of a processor of a second embodiment.

Next, a description will be given of a method of calculating the mass concentration performed by the processor 36 of the measurement device 102. FIG. 9 illustrates a flowchart of an operation of the processor of the second embodiment. As illustrated in FIG. 2, the processor 36 calculates the hygroscopic parameter of the particles 10a in the gas 80a as illustrated in FIG. 4 (step S70). The processor 36 obtains the number concentration of the particles 10b in the gas 80b measured by the concentration measurer 68 of light scattering type (step S72). The concentration measurer 68 of light scattering type measures the number concentration of the particles 10b in the gas 80b having desirable sizes. It is preferable that the sizes of the particles 10b are approximately the same as those of the particles 10a separated by the impactor 44. The processor 36 obtains the humidity of the gas 80b measured by the humidity sensor 69 (step S74). The processor 36 calculates the mass concentration of the particles 10b of the gas 80b based on the number concentration, the humidity and the hygroscopic parameter (step S76).

A description will be given of a method of calculating the mass concentration performed by the processor 36. When the number concentration measured by the concentration measurer 68 of light scattering type is Cn and a mass concentration to be calculated is Cm, the mass concentration Cm is expressed by the following formula with use of the number concentration Cn, the humidity h and the hygroscopic parameter a(h).

$$Cm = k \cdot Cn \cdot a(h)$$

"k" is a correction constant and is obtained by studying a correlation among the Cm obtained by the method of collecting the particles with use of a filter or a beta-ray absorption method, the Cn obtained by the light scattering detection method, and the humidity. When "k" is obtained, the Cm can be calculated from the Cn and the a(h).

The processor 36 waits for a predetermined time (step S78). The processor 36 determines whether to measure the hygroscopic parameter (step S80). The processor 36 determines as "Yes" when a predetermined time has passed from the previous measuring of the hygroscopic parameter. When it is determined as "Yes", the step S70 is executed again. When it is determined as "No", the processor 36 determines whether to terminate the flowchart (step S82). When it is determined as "Yes", the flowchart is terminated. When it is determined as "No", the step S72 is executed again.

The concentration measurer 68 of light scattering type is capable of measuring the concentration with a high frequency. For example, the number concentration can be measured every one minute. It takes at least ten minutes to measure the hygroscopic parameter. Therefore, the concentration measurer 68 of light scattering type measures the hygroscopic parameter at an interval of one hour or one day or the like for a period when the components of the particles 10a do not change. That is, the frequency of the measuring of the number concentration performed by the concentration measurer 68 of light scattering type is higher than the frequency of the changing of the humidity performed by the humidity adjuster 38. Thus, the mass concentration can be measured with a high frequency.

Third Embodiment

Figure 10:
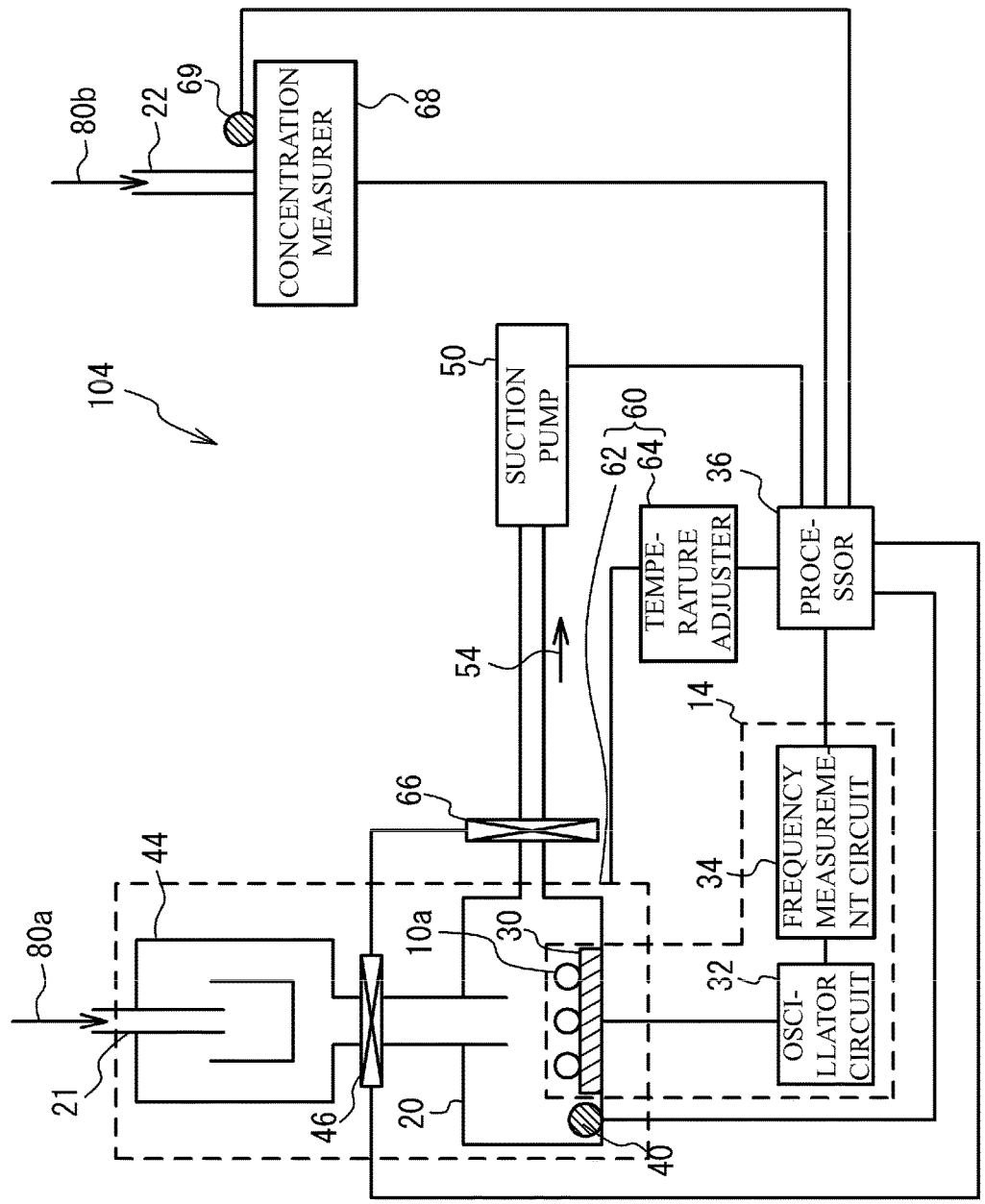
FIG. 10 illustrates a block diagram of a measurement device in accordance with a third embodiment.

A third embodiment is an example where humidity is changed by changing a temperature of gas. FIG. 10 illustrates a block diagram of a measurement device in accordance with the third embodiment. In the third embodiment, in a measurement device 104, a humidity adjuster 60 has a temperature adjuster container 62 and a temperature adjuster 64. The temperature adjuster container 62 surrounds the impactor 44 and the measurement tank 20, and adjusts the temperature of the atmosphere in the measurement tank 20. The temperature adjuster 64 adjusts the temperature with use of the temperature adjuster container 62. An isolation valve 66 is provided between the measurement tank 20 and the suction pump 50. Other structures are the same as FIG. 3 of the second embodiment. Therefore, an explanation of the structures is omitted.

In the third embodiment, in the step S34 of FIG. 5, the processor 36 sweeps the humidity in the measurement tank 20 by sweeping the temperature in the temperature adjuster container 62. The step S22 of FIG. 4 is performed as follows.

Figure 11:
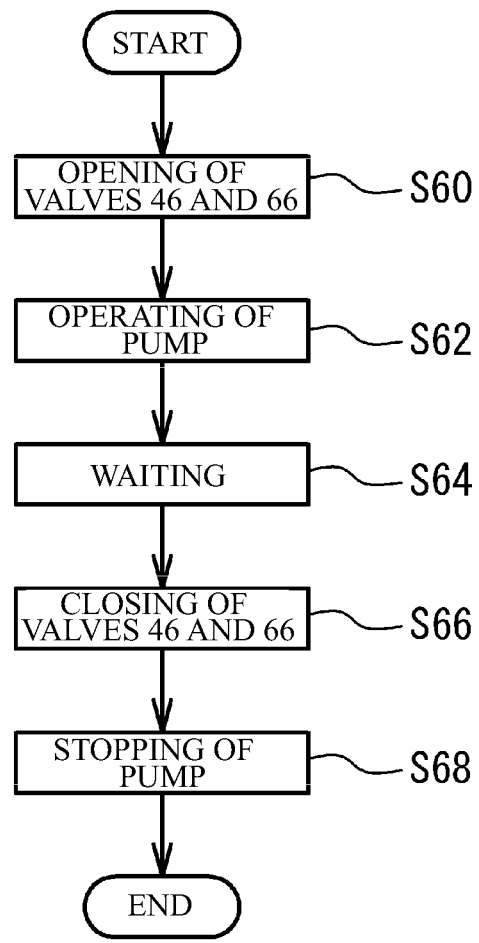
FIG. 11 illustrates a flowchart of step S22 of FIG. 4 in accordance with a third embodiment.

FIG. 11 illustrates a flowchart of the step S22 of FIG. 4 in accordance with the third embodiment. As illustrated in FIG. 11, the processor 36 opens the isolation valves 46 and 66 (step S60). The processor 36 operates the suction pump 50 (step S62). Thus, the particles 10a having desirable sizes are provided into the measurement tank 20. The processor 36 waits for a predetermined time (step S64). The processor 36 closes the isolation valves 46 and 66 (step S66). The processor 36 stops the suction pump 50 (step S68). With the processes, the collection of the particles 10a is terminated.

Figure 12A:
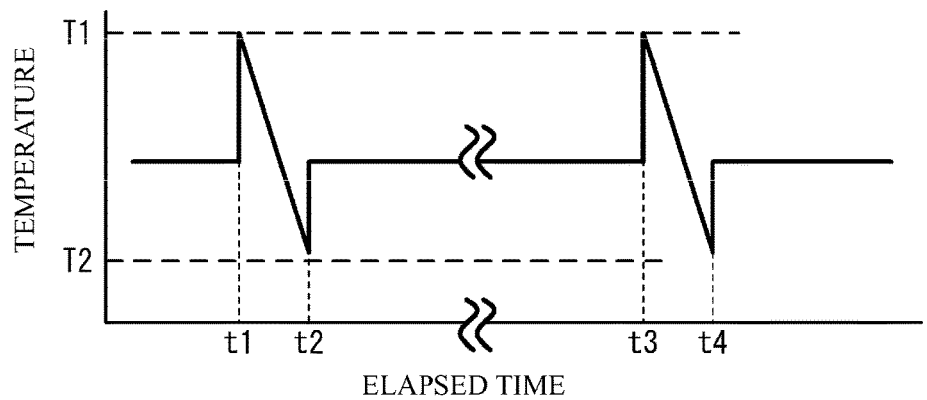
FIG. 12A to FIG. 12C respectively illustrate a temperature, relative humidity and a mass with respect to an elapsed time.
Figure 12B:
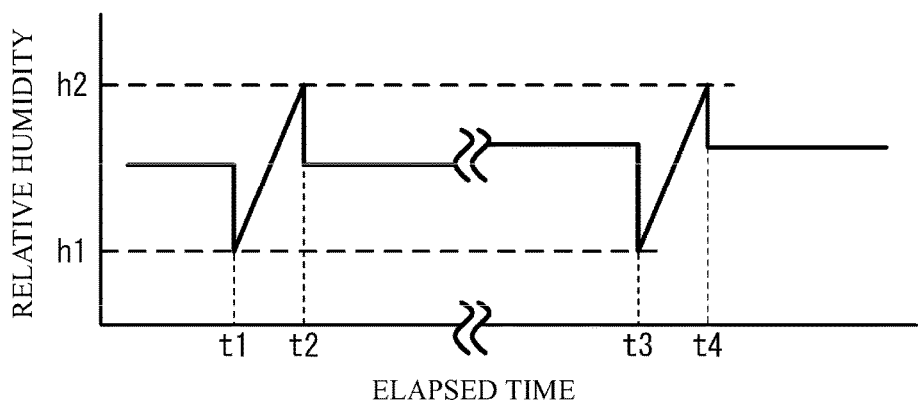
Figure 12C:
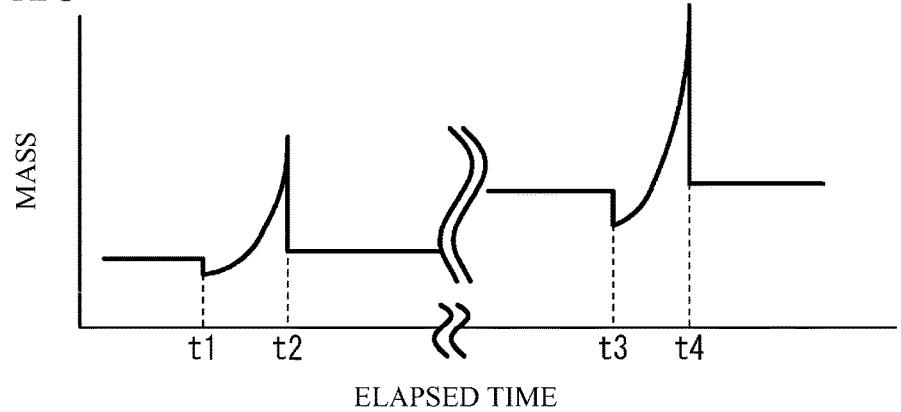

FIG. 12A to FIG. 12C respectively illustrate the temperature, the relative humidity and the mass with respect to the elapsed time. As illustrated in FIG. 12A to FIG. 12C, until the time t1, the temperature in the measurement tank 20 is not adjusted, and the temperature and the humidity in the measurement tank 20 are not constant. From the time t1 to the time t2, the measurement of the step S20 is performed. At the time t1, the temperature adjuster 64 starts to change the temperature in the measurement tank 20. The temperature in the measurement tank 20 is T1 and the relative humidity is h1 at the time t1. The temperature gradually changes from the time t1 to the time t2. The temperature is T2 and the relative humidity is h2 at the time t2.

From the time t2 to the time t3, the particles 10a are collected on the quartz crystal oscillator 30 as in the case of the step S22. From the time t3 to the time t4, the measuring of the step S24 is performed. From the time t3 to the time t4, the temperature in the measurement tank 20 changes from T1 to T2, and the humidity continuously changes from h1 to h2. With the changing of the humidity, the mass of the quartz crystal oscillator 30 changes.

When the temperature of the measurement tank 20 changes, the isolation valves 46 and 66 are being closed as illustrated in FIG. 11 and there is no movement of air in and out of the measurement tank 20. Therefore, an amount of steam in the measurement tank 20 is constant. Therefore, when the temperature is changed, the humidity is also changed. The oscillation frequency of the quartz crystal oscillator changes with the changing of the temperature. Therefore, when the mass of FIG. 12C is calculated, a correlation between the temperature and the oscillation frequency is measured in advance, and the oscillation frequency is corrected with use of the correlation.

The processor 36 calculates the hygroscopic parameter of the particles 10a, similarly to FIG. 8A to FIG. 8C of the second embodiment.

In the second embodiment, the humidity adjuster 38 performs dehumidifying and humidifying. Therefore, the humidity adjuster 38 has a large size. It is necessary to supply water for the humidifying. This may cause obstacle to an unattended operation. In the third embodiment, the humidity changer changes the humidity of the atmosphere by changing the temperature of the atmosphere in the measurement tank 20. Thus, it is not necessary to provide the humidity adjuster 38 of the second embodiment. It is therefore possible to downsize the device. And, an automatic operation becomes easier.

Figure 13A:
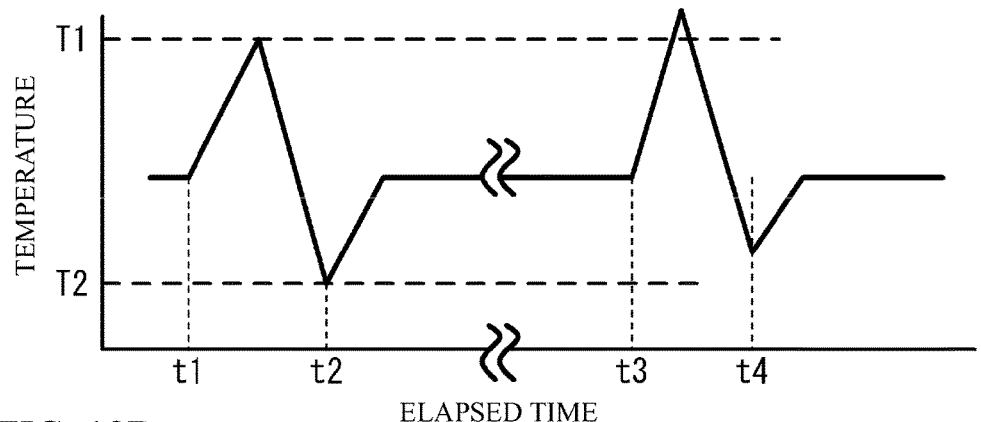
FIG. 13A to FIG. 13C respectively illustrate another temperature, another relative humidity and another mass with respect to an elapsed time.
Figure 13B:
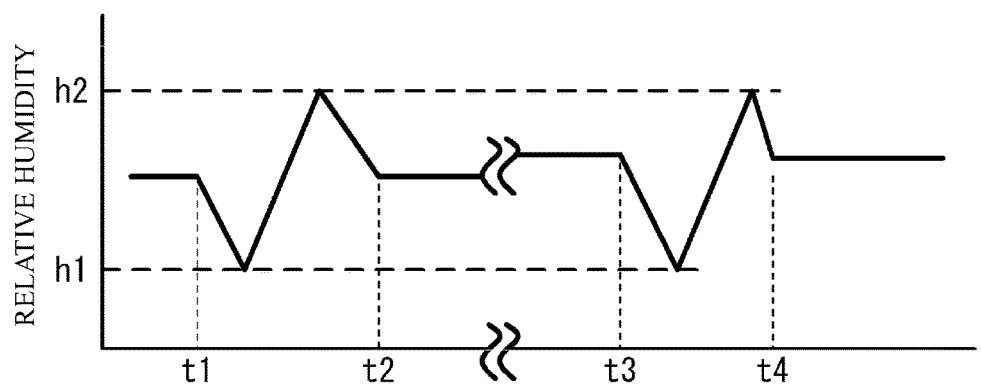
Figure 13C:
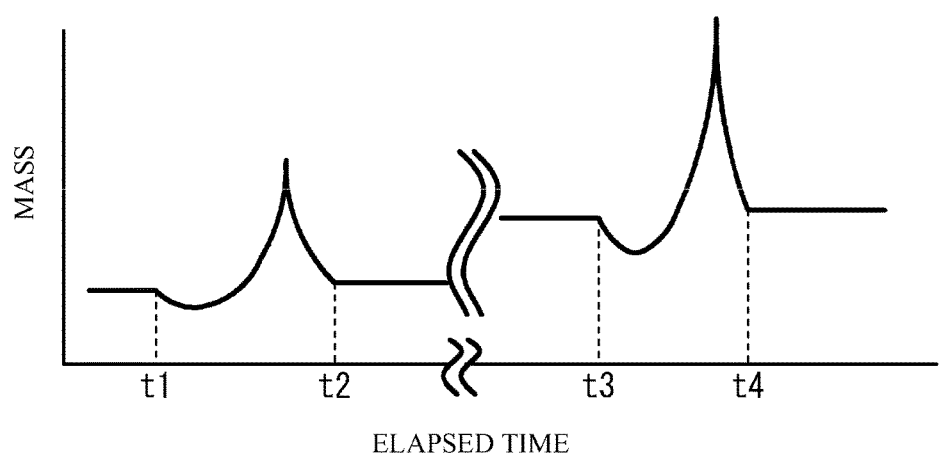

FIG. 13A to FIG. 13C respectively illustrate another temperature, another humidity and another mass with respect to the elapsed time. As illustrated in FIG. 13A to FIG. 13C, from the time t1 to the time t2, and from the time t3 to the time t4, a correlation between the humidity and the mass is obtained when increasing the temperature and decreasing the temperature. Similarly to FIG. 8A to FIG. 8C, the hygroscopic parameter during the increasing of the humidity and the hygroscopic parameter during the decreasing of the humidity are calculated.

According to the type of the components of the particles, a hysteresis may occur in the curve between the moisture absorption amount and the humidity. In this case, the hygroscopicity during the increasing of the humidity is different from the hygroscopicity during the decreasing of the humidity. In the examples of FIG. 13A to FIG. 13C, different hygroscopic parameters may be used during the increasing of the humidity and the decreasing of the humidity. It is therefore possible to performing the measuring with higher accuracy. In the second embodiment, a hygroscopic parameter during the increasing of the humidity and another hygroscopic parameter during the decreasing of the humidity may be calculated.

In the first to third embodiments, the measurement device for measuring the hygroscopic parameter may be separated from the measurement device for measuring the mass concentration. That is, it is not necessary for the measurement device for measuring the hygroscopic parameter to measure the number concentration of the particles. The measurement device for measuring the mass concentration may measure the mass concentration with use of the hygroscopic parameter measured by another measurement device without measuring the hygroscopic parameter. The humidity in the present specification is a relative humidity.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various change, substitutions, and alterations could be made hereto without departing from the spirit and scope of the invention.

What is claimed is:

1. A measurement device, comprising:
   a tank into which gas is introduced from an atmosphere;
   a humidity changer that changes humidity of the gas in the tank;
   a humidity sensor that measures the humidity of the gas in the tank;
   a mass measurer that measures mass of particles being adsorbed on a surface of a quartz crystal oscillator installed in the tank;
   a concentration measurer that measures repeatedly a number concentration of particles in the atmosphere; and
   a processor that acquires a function indicating a correlation of the mass of particles in the gas introduced into the tank with respect to the humidity changed by changing the humidity of the gas in the tank, and calculates a mass concentration of the particles in the atmosphere on the basis of the function, the number concentration, and humidity of the atmosphere,
   wherein the processor repeatedly acquires the function each time the number concentration is measured, and repeatedly calculates the mass concentration on the basis of the measured number concentration, the humidity of the atmosphere, and a function acquired immediately before calculating the mass concentration among repeatedly acquired functions;
   a frequency of calculating the function is lower than a frequency of calculating the mass concentration.

2. The measurement device as claimed in claim 1, wherein the concentration measurer measures the number concentration with use of a light scattering detection method.

3. The measurement device as claimed in claim 1, wherein the humidity changer changes the humidity of the gas in the tank by heating or cooling the tank.

4. The measurement device as claimed in claim 1, wherein the humidity changer continuously changes the humidity of the gas in the tank.

5. The measurement device as claimed in claim 1, wherein the humidity changer continuously increases or continuously decreases the humidity of the gas in the tank.

6. The measurement device as claimed in claim 1, further comprising:
   another humidity sensor that measures the humidity of the atmosphere, wherein the concentration measurer and the another humidity sensor respectively perform measuring of the number concentration of the particles in the atmosphere and measuring of the humidity of the atmosphere simultaneously.

7. The measurement device as claimed in claim 1, further comprising:
   another humidity sensor that measures the humidity of the atmosphere.

8. The measurement device as claimed in claim 1, wherein the processor calculates the function each time the mass concentration of particles is calculated multiple times, and calculates the mass concentration of the particles using a function acquired immediately before calculating the mass concentration among repeatedly acquired functions.

9. A method of measuring, comprising:
   introducing gas into a tank from an atmosphere;
   measuring humidity of the gas in the tank;
   measuring mass of particles being adsorbed on a surface of a quartz crystal oscillator installed in the tank;
   measuring a number concentration of particles in the atmosphere repeatedly;
   measuring humidity of the atmosphere;
   changing the humidity of the gas in the tank;
   acquiring a function indicating a correlation of the mass of particles in the gas introduced into the tank with respect to the humidity changed by changing the humidity of the gas in the tank; and
   calculating a mass concentration of the particles in the atmosphere on the basis of the function, the number concentration, and humidity of the atmosphere,
   wherein the acquiring the function is repeatedly executed each time the number concentration is measured, and the calculating the mass concentration is repeatedly executed on the basis of the measured number concentration, the humidity of the atmosphere, and a function acquired immediately before calculating the mass concentration among repeatedly acquired functions;
   a frequency of calculating the function is lower than a frequency of calculating the mass concentration.

* * * * *